(12) United States Patent
Mahon et al.

(10) Patent No.: US 11,406,303 B2
(45) Date of Patent: Aug. 9, 2022

(54) SYSTEMS AND METHODS FOR PREVENTING CONTAMINATION OF RECORDED BIOLOGICAL SIGNALS DURING SURGERY

(71) Applicant: SafeOp Surgical, Inc., Stamford, CT (US)

(72) Inventors: Cameron Mahon, Hunt Valley, MD (US); Curt Labelle, Hunt Valley, MD (US)

(73) Assignee: SafeOp Surgical, Inc., Stamford, CT (US)

(*) Notice: Subject to any disclaimer, the term of this patent is extended or adjusted under 35 U.S.C. 154(b) by 306 days.

(21) Appl. No.: 16/535,840

(22) Filed: Aug. 8, 2019

(65) Prior Publication Data
US 2019/0357789 A1 Nov. 28, 2019

Related U.S. Application Data

(62) Division of application No. 15/025,259, filed as application No. PCT/US2014/058494 on Sep. 30, 2014, now Pat. No. 10,376,167.
(Continued)

(51) Int. Cl.
*A61B 5/00* (2006.01)
*A61B 5/24* (2021.01)
(Continued)

(52) U.S. Cl.
CPC .............. *A61B 5/24* (2021.01); *A61B 5/377* (2021.01); *A61B 5/4041* (2013.01); *A61B 5/725* (2013.01);
(Continued)

(58) Field of Classification Search
CPC ... A61B 5/04001; A61B 5/725; A61B 5/4041; A61B 5/0484; A61N 1/20; A61N 1/0456; A61N 1/0551
See application file for complete search history.

(56) References Cited

U.S. PATENT DOCUMENTS

| 4,161,945 A | 7/1979 | Grossman |
| 4,863,265 A | 9/1989 | Flower |

(Continued)

FOREIGN PATENT DOCUMENTS

| CN | 102368951 A | 3/2012 |
| CN | 102824170 A | 12/2012 |

(Continued)

OTHER PUBLICATIONS

Doemges, et al., Changes in the stretch reflex of the human first dorsal interosseous muscle during different tasks Journal of Physiology, 1992, pp. 563-573, vol. 447.

*Primary Examiner* — Daniel L Cerioni
*Assistant Examiner* — Raymond P Dulman
(74) *Attorney, Agent, or Firm* — Mintz, Levin, Cohn, Ferris, Glovsky and Popeo, P.C.

(57) ABSTRACT

A system for recording, processing, and monitoring biosignals is provided, the system being configured to suspend data acquisition whenever an electric surgical tool or other generator of high frequency interference is in use. Such a system may protect the hardware of the system and reduce or eliminate the acquisition of distorted signals. The system of some embodiments includes an amplifier system configured to detect the presence of high frequency interference. Related methods are also disclosed.

20 Claims, 7 Drawing Sheets

Related U.S. Application Data

(60) Provisional application No. 61/884,525, filed on Sep. 30, 2013.

(51) Int. Cl.
*A61B 5/377* (2021.01)
*A61N 1/04* (2006.01)
*A61N 1/20* (2006.01)
*A61B 17/00* (2006.01)

(52) U.S. Cl.
CPC .......... *A61B 5/7217* (2013.01); *A61N 1/0456* (2013.01); *A61N 1/20* (2013.01); *A61B 2017/00026* (2013.01)

(56) References Cited

U.S. PATENT DOCUMENTS

| | | |
|---|---|---|
| 4,934,377 A | 6/1990 | Bova |
| 5,662,105 A | 9/1997 | Tien |
| 6,067,467 A | 5/2000 | John |
| 6,391,024 B1 | 5/2002 | Sun |
| 6,535,767 B1 | 3/2003 | Kronberg |
| 6,556,861 B1 | 4/2003 | Prichep |
| 6,985,833 B2 | 1/2006 | Shambroom |
| 7,620,453 B1 | 11/2009 | Propato |
| 7,904,160 B2 | 3/2011 | Brodnick |
| 8,108,039 B2 | 1/2012 | Saliga |
| 8,515,530 B2 | 8/2013 | Warner |
| 8,538,512 B1 | 9/2013 | Bibian |
| 8,731,654 B2 | 5/2014 | Johnson |
| 10,376,167 B2 | 8/2019 | Mahon et al. |
| 2003/0052775 A1 | 3/2003 | Shambroom |
| 2003/0083719 A1 | 5/2003 | Shankar |
| 2005/0228306 A1 | 10/2005 | Kurtz |
| 2007/0225674 A1 | 9/2007 | Molnar |
| 2007/0282217 A1* | 12/2007 | McGinnis .............. A61B 5/389 600/546 |
| 2008/0051844 A1 | 2/2008 | Brodnick et al. |
| 2009/0124869 A1 | 5/2009 | Hu |
| 2009/0143693 A1 | 6/2009 | Ye |
| 2010/0036211 A1 | 2/2010 | La Rue |
| 2010/0198099 A1 | 8/2010 | Murphy |
| 2010/0274144 A1 | 10/2010 | Hu |
| 2011/0224570 A1 | 9/2011 | Causevic |
| 2011/0224988 A1 | 9/2011 | Mahajan |
| 2012/0165690 A1 | 6/2012 | Chen |
| 2012/0313757 A1 | 12/2012 | Volpi |
| 2013/0024524 A1 | 1/2013 | Graff et al. |
| 2013/0245424 A1 | 9/2013 | Decharms |
| 2015/0061758 A1* | 3/2015 | Hsu ..................... G06K 9/0051 327/553 |
| 2016/0228018 A1 | 8/2016 | Mahon et al. |

FOREIGN PATENT DOCUMENTS

| | | |
|---|---|---|
| CN | 102883775 A | 1/2013 |
| JP | S51-154986 U | 12/1976 |
| JP | S59-022106 U | 2/1984 |
| JP | S5922106 A | 2/1984 |
| JP | S59193403 A | 11/1984 |
| JP | S59-193403 U | 12/1984 |
| JP | H04253843 A | 9/1992 |
| JP | H06277189 A | 10/1994 |
| JP | H06277189 A | 10/1994 |
| JP | 2003131668 A | 5/2003 |
| JP | 2005073223 A | 3/2005 |
| JP | 2005519646 A | 7/2005 |
| JP | 2007185326 A | 7/2007 |
| JP | 2009071387 A | 4/2009 |
| JP | 2010104586 A | 5/2010 |
| JP | 5466389 B2 | 4/2014 |
| WO | WO-2003000128 A2 | 1/2003 |
| WO | 2015048822 A1 | 4/2015 |

* cited by examiner

SYSTEMS AND METHODS FOR PREVENTING CONTAMINATION OF RECORDED BIOLOGICAL SIGNALS DURING SURGERY

CROSS-REFERENCE TO RELATED APPLICATIONS

This application is divisional of U.S. application Ser. No. 15/025,259, filed Mar. 25, 2016, which is a National Stage of International Application No. PCT/US2014/058494, filed Sep. 30, 2014, which claims the benefit of U.S. Provisional Patent Application No. 61/884,525 entitled "MEANS OF PREVENTING CONTAMINATION OF SSEP SIGNALS DURING SURGERY" filed on Sep. 30, 2013, the disclosures of which are expressly incorporated by reference herein in their entirety.

FIELD

The present technology relates generally to the field of electrophysiology. In particular, the technology relates to devices, systems, and methods for filtering out noise during the recording and/or processing of biosignals.

BACKGROUND

Eliciting and tracking evoked potentials during surgery is an established method for monitoring for potential nerve injuries. For example, electrically stimulating a patient during surgery and monitoring the resultant somatosensory evoked potentials (SSEPs) using conventional intraoperative neurophysiologic monitoring (IONM) systems is an accepted and useful clinical procedure that can identify changes in brain, spinal cord, and peripheral nerve function. Conventional IONM systems are typically used when the risk of severe nerve damage is relatively high, such as, for example, during brain and spinal surgeries. Early and accurate identification of changes in nervous system functioning may minimize the occurrence of long-term damage to structures of the nervous system.

Similarly, improved neurophysiologic monitoring devices and methods have been developed, which can be used to stimulate and monitor a patient's evoked potentials during other surgeries in order to identify and prevent positioning effect injuries. Such devices and methods are described in U.S. Pat. No. 8,731,654 to Johnson et al., the disclosure of which is herein incorporated by reference in its entirety. Positioning effect injury is an injury caused by undue tension or pressure on peripheral nervous structures. It can be caused by the position in which a patient is placed during surgery. Warning signs of positioning effect may include sensations, such as, for example, numbness, tingling, or weakness in a portion of the body. During surgery, a patient is typically placed under general anesthesia and unable to identify or react to the usual warning signs of positioning effect. Consequentially, patients may be left in compromised positions for the duration of a surgical procedure. Continued trauma from positioning effect may result in prolonged or even permanent injury to one or more peripheral nerves.

Intraoperative neurophysiologic monitoring is generally performed with a specialized computing device that delivers electrical stimulations to a patient's body and records signals produced by the body in response. Alternatively, spontaneously arising signals that do not require stimulation may be recorded. The specialized computing device typically performs some processing of the recorded signal(s), and healthcare professionals may monitor the processed signal for changes.

In order for monitoring to be effective noise and interference should be minimized. Reducing noise and interference is a particular concern when the target signals are very small such as with evoked potentials, because even the presence of a little noise can dramatically reduce the signal-to-noise ratio due to the small size of evoked potentials. Evoked potentials, such as, for example, SSEPs, are small bioelectric signals with amplitudes as small as one microvolt or less.

Techniques have been developed to reduce random noise present in processed biosignals. Unfortunately, current techniques are not sufficient. Interference remaining in the processed signal when using current techniques can significantly distort the processed signal. Accordingly, there is a need for improved signal acquisition and/or processing systems and techniques capable of further reducing or eliminating interference in the processed signal.

SUMMARY

There is a significant need for improved intraoperative electrophysiological monitoring devices and methods that enable reliable acquisition and display of desired biological signals. There is a need for medical devices capable of acquiring and displaying waveforms that accurately and precisely match biological signals generated by a patient's body in response to stimuli. There is a need for signal processing devices and methods that eliminate or substantially eliminate the presence of electrical interference, caused by electrical surgical devices, within processed signals. Embodiments provided herein may address one or more of these needs.

Embodiments described herein generally relate to improved devices, components, systems, and methods for acquiring and isolating evoked potential signals and/or other biosignals detected during surgery. Various embodiments relate to devices, systems, and methods for processing a recorded signal in such a manner that interference from electric surgical devices is reduced or eliminated while the target biosignal is maintained.

One aspect of the disclosure relates to methods for detecting changes in nerve functioning within a subject. The methods can utilize any of the devices, apparatuses and systems described herein. The methods can include receiving one or more biosignals, such as evoked potentials, from a patient, as an input at a biosignal detection device. The methods can further include obtaining a processed signal having minimal electronic interference or background noise contaminating the processed signal, wherein such a processed signal is obtained by reducing, blocking, ignoring, or disregarding detected signals received when high frequency electronic interference or background noise is present. The methods can further include comparing at least two processed signal received at different time periods, and identifying a change in the biosignals based upon the comparison of the at least two processed signals. In some embodiments, the biosignals can be evoked potentials from peripheral nerves. In some embodiments, the methods can further include detecting a nerve injury during a medical procedure or while a subject is not conscious, including, but not limited to a positioning effect based on changes observed between the at least two processed signals.

Another aspect of the disclosure is directed to a method performed by an amplifier system within a biosignal monitoring device. In various embodiments, the method includes:

receiving a threshold level input from a user via a user interface; receiving a first detected signal along a first signal line, wherein the first detected signal comprises a target biosignal and high frequency noise; filtering the first detected signal to reduce the high frequency noise in the first detected signal; amplifying the first detected signal to increase a magnitude of the biosignal; converting the first detected signal from analog to digital for data acquisition by a microprocessor; receiving a second detected signal along a second signal line, wherein the second detected signal comprises the target biosignal and the high frequency noise; comparing the second detected signal to the threshold level to determine whether the second detected signal or the threshold level is greater; and upon detecting that the second detected signal is greater than the threshold level, performing one or more steps to suspend acquisition of the first detected signal.

In some embodiments, the one or more steps performed to suspend acquisition of distorted signals includes: suspending acquisition and storage of digital data by a microprocessor, wherein the digital data is received from an analog to digital converter of the first signal line, and wherein the digital data is a digitized first detected signal. Additionally or alternatively, in some embodiments, the one or more steps performed to suspend acquisition of distorted signals comprises: transmitting an interrupt signal along a control line to an amplifier within the first signal line, wherein the interrupt signal causes the amplifier to temporarily suspend operation. In some such embodiments, the amplifier suspends operation for approximately 5 to approximately 60 seconds. In other embodiments, the amplifier suspends operations until the second detected signal is no longer detected to be greater than the threshold level, or until a defined time thereafter. In other embodiments, the amplifier suspends operation until transmission of the interrupt signal ceases.

Another aspect of the disclosure is directed to a non-transitory computer readable medium, which stores instructions. In some embodiments, the instructions, when implemented, cause a processor to perform a method, such as, for example, an embodiment of the method described above.

A further aspect of the disclosure is directed to an automated device for isolating a target evoked potential or other biosignal from high frequency noise present in a recorded signal. In some embodiments, the device includes a non-transitory computer readable medium, such as the computer readable medium described above or elsewhere in this disclosure. In some embodiments, the device further includes: a processor configured to execute instructions stored on the non-transitory computer readable medium; a signal input configured to couple to a recording electrode; and a data output configured to send processed data to a user interface.

An additional aspect of the disclosure is directed to an amplifier system. In various embodiments, the amplifier system comprises a first signal pathway and a second signal pathway, each signal pathway having an input for a detected signal, wherein the detected signal comprises a target signal and high frequency interference. The first signal pathway is configured to amplify the target signal. In various embodiments, the first signal pathway includes, at least: a low pass filter, an amplifier, an analog to digital converter, and a microprocessor. In various embodiments, the low pass filter output is electrically coupled to the amplifier, the amplifier output is electrically coupled to the analog to digital converter (ADC), and the ADC output is electrically coupled to the microprocessor. The second signal pathway is configured to detect the high frequency interference. In various embodiments, the second signal pathway includes, at least: a band pass filter or high pass filter electrically coupled to a radiofrequency detector, a comparator, a digital to analog converter, and the microprocessor of the first signal pathway. The comparator of various embodiments is configured to compare signal sizes of a first signal entering from a first leg and a second signal entering from a second leg, the first leg of the comparator being electrically coupled to an output from the radiofrequency detector, and the second leg being electrically coupled via the digital to analog converter to an output from the microprocessor. In various embodiments, the microprocessor is electrically coupled to an output from the comparator and is configured to detect the presence of high frequency interference within the detected signal when the first signal is greater than the second signal.

In some embodiments of the amplifier system, the second signal is a threshold signal set by a user interacting with the microprocessor via a user interface.

In some embodiments, the amplifier system is configured to temporarily suspend signal amplification upon detection of high frequency interference. Additionally or alternatively, in some embodiments, the amplifier system is configured to temporarily suspend data acquisition upon detection of high frequency interference. In some embodiments, the amplifier system additionally includes a control line electrically connecting the microprocessor to the amplifier of the first signal pathway, wherein the control line is configured to deliver an interrupt signal to the amplifier upon detection of high frequency interference.

In some embodiments, the amplifier system further includes one or more low pass filters positioned between the comparator and the microprocessor. In some embodiments, the band pass filter of the second signal pathway is formed of, or includes, one or more inductors, capacitors, or a combination thereof, configured to pass a frequency band of interest while eliminating signals outside the frequency band of interest. In some such embodiments, the frequency band of interest is 200 kHz to 6 MHz.

In some embodiments of the amplifier system, the radiofrequency detector is formed of, or includes, an ultrafast diode, a capacitor connected to ground, and a parallel shunt resistor connected to ground.

In some embodiments, the target signal is a biological signal. In at least some such embodiments, the biological signal is an evoked potential.

Yet another aspect of the disclosure is directed to a system for recording a non-distorted evoked potential. In various embodiments, the system includes: a signal output operable to couple directly or indirectly to a stimulating electrode to deliver an electrical stimulus to a body; a signal input operable to couple directly or indirectly to a recording electrode to receive a detected signal, wherein the detected signal includes high frequency interference and an evoked potential generated by the body's nervous system in response to the electrical stimulus; and a processing circuit coupled to the signal input. In various embodiments, the processing circuit includes: a microprocessor configured to process and analyze a recorded signal, and an amplifier system. The amplifier system includes: a first signal path configured to amplify the evoked potential, and a second signal path configured to detect the high frequency interference. In various embodiments, the first signal path and the second signal path are both connected to the microprocessor, and the microprocessor is further configured to suspend data acquisition from the first signal path and suspend amplification within the amplifier of the first signal path upon detection of high frequency interference within the detected signal.

In some embodiments of the system, the first signal path includes only or at least: a low pass filter, an amplifier, an analog to digital converter, and the microprocessor. In some embodiments, the second signal path includes a band pass filter, a radiofrequency detector, a comparator, one or more low pass filters, a digital to analog converter, and the microprocessor.

DETAILED DESCRIPTION

Figure 1:
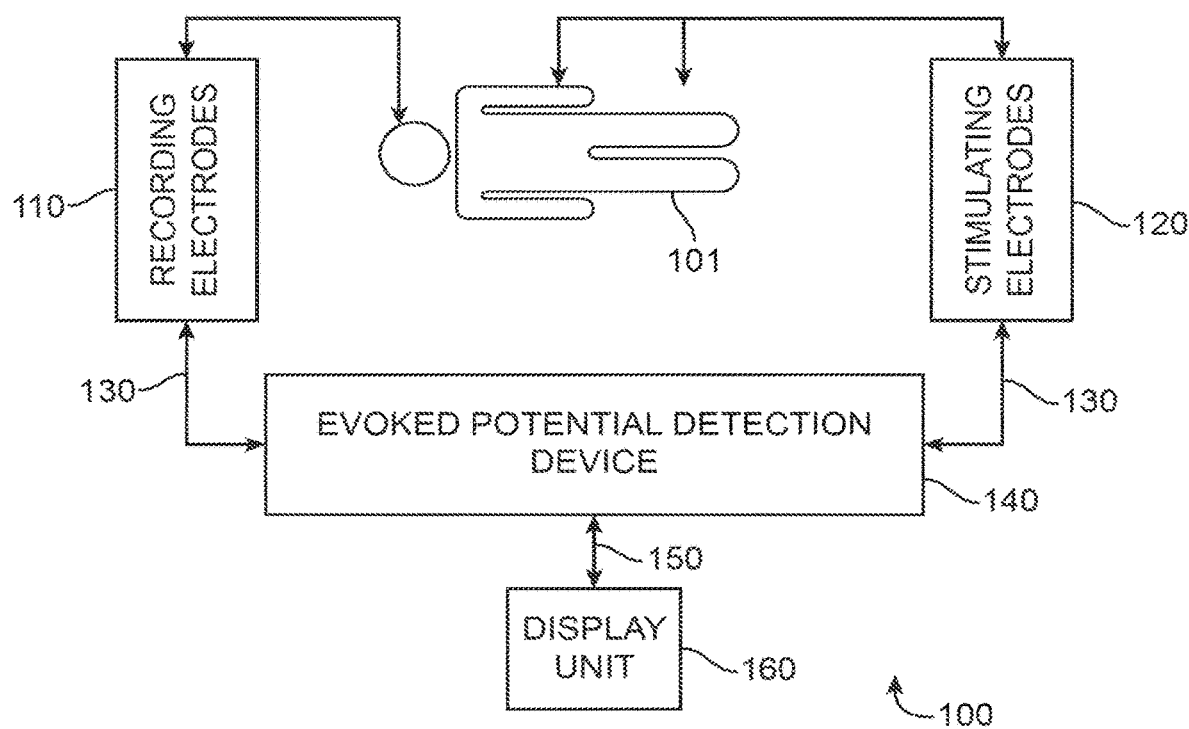
FIG. 1 depicts a functional block diagram of one embodiment of a system for monitoring nerve function.

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Definitions

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

The term "substantially," when used in the context of substantially eliminating electrical interference, shall mean eliminating at least 80%, at least 90%, at least 95%, or at least 99% of the interference present in a detected signal.

As used in the specification and claims, the singular form "a", "an", and "the" include both singular and plural references unless the context clearly dictates otherwise. For example, the term "an evoked potential" may include, and is contemplated to include, a plurality of evoked potentials. At times, the claims and disclosure may include terms such as "a plurality," "one or more," or "at least one;" however, the absence of such terms is not intended to mean, and should not be interpreted to mean, that a plurality is not conceived for a particular embodiment.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

"Biosignal" or "biological signal" shall refer to any detectable waveform generated from a living body, such as, for example, an evoked potential, an EEG, EMG, or ECG.

"Evoked potential" shall mean any electrical potential recorded from the nervous system, which results from the application of a stimulus to a portion of the body. Evoked potentials include, for example, somatosensory evoked potentials (SSEPs), visual evoked potentials (VEPs), motor evoked potentials (MEPs), and brain stem auditory evoked potentials (BAEPs).

"Somatosensory evoked potentials," also known as "SSEPs" or "SEPs," and referred to herein as "SSEPs," shall refer to electrical signals generated by the nervous system in response to an electrical stimulation of a peripheral nerve.

One of ordinary skill in the art will appreciate that while many embodiments disclosed herein are described in the context of detection and isolation of SSEPs for the sake of simplicity of the description, various embodiments may also detect MEPs, VEPs, other evoked potentials, and/or other biosignals.

System Overview

Various embodiments provided herein are directed to improved systems, components, and methods for detecting and recording biosignals, such as evoked potentials, that are free of distortion from high frequency interference. FIG. 1 depicts a block diagram of a system 100 for automatically detecting evoked potentials in accordance with one embodiment of the present disclosure. As described in more detail below, the system 100 may include circuitry and/or other components that significantly improve the system's ability to acquire clean evoked potentials free of high frequency interference. In the depicted embodiment, the system 100, which may be coupled to a patient 101, includes, but is not limited to, one or more recording electrodes 112, one or more stimulating electrodes 122, an evoked potential detection device (EPDD) 140, and a display unit 160. The stimulating and recording electrodes are each positioned over, near, in contact with, and/or around a nervous system structure, such as the brain, the spinal cord, or a nerve. The electrodes may be needle electrodes, surface electrodes, cuff electrodes, or any other suitable electrode type.

In various embodiments, the EPDD 140 is electronically coupled to the recording electrodes 112 and stimulating electrodes 122 via a plurality of cables 130. The EPDD 140 of various embodiments forms part of, is coupled to, and/or includes a computer, such as, for example, the computer described in further detail with reference to FIG. 7. As described in the discussion of FIG. 7, the specialized computing device includes a processor and memory and stores programmed instructions. The instructions, when executed by the processor, cause the device to: (1) deliver stimulations (in the form of electric current or voltage) to the stimulating electrodes, and (2) record detected signals picked up at the recording electrodes.

In various embodiments, the stimulating electrode 122 may be incorporated into the EPDD 140, coupled to the EPDD 140, or attachable, directly or indirectly to the EPDD 140. According to an exemplary embodiment, the EPDD 140 sequentially stimulates one or more peripheral nerves via the stimulating electrode 122 while recording the SSEPs via the recording electrode 112. According to an exemplary embodiment, the EPDD 140 includes an output operable to couple to the stimulating electrodes 122. The recording electrodes 112 of various embodiments may be incorporated into the EPDD 140, coupled to the EPDD 140, or attachable, directly or indirectly to the EPDD 140. According to an exemplary embodiment, the EPDD 140 includes an input operable to couple the EPDD 140 to the recording electrode 112.

The specialized computing device processes the recorded signal and transmits data indicative of the processed signal to a display unit 160 for display. Healthcare professionals may then monitor the display for changes in the processed signal. In various embodiments, the EPDD 140 is electrically, electronically, and/or mechanically coupled to the display unit 160 via a link 150. In some embodiments, the link 150 is internal wiring or external cable. In some embodiments, the link 150 is a wireless communication link. For example, in some embodiments, the EPDD 140 is wirelessly coupled to the display unit 160 via Bluetooth® or other radiofrequency signal or via near field communications or a cellular signal.

According to an exemplary embodiment, the system 100 is configured to monitor SSEPs. In one such embodiment, the stimulating electrodes 122 are configured for placement on the arms or legs of a patient 101 over peripheral nervous structures such as, for example, the ulnar nerves, median nerves, peroneal nerves, and/or posterior tibial nerves. In some embodiments, the stimulating electrodes 122 are intended for placement at the wrists and/or ankles of a patient so that the electrodes are located over, on, adjacent to, or near the ulnar nerves and/or posterior tibial nerves.

The recording electrodes 112 of some embodiments are configured for placement at the trunk, spine, neck, and/or head. In some embodiments, the recording electrodes 112 are intended to be placed on, at, over, or near one or more of the following locations: the scalp, cervical vertebra, the forehead, the left and right Erb's points near the clavicle, and the left and right Popliteal Fossa just above the knee, or other points of nerve transmission that allow recording.

According to an exemplary embodiment, the EPDD 140 applies electrical stimulation to peripheral nerves of a patient by sending electrical pulses to the stimulating electrodes 122 located on some or all of a patient's limbs. Repeated stimulation elicits a response of the patient's nervous system in the form of SSEPs, which travel up the peripheral nerves, through the dorsal column of the spinal cord, and to the brain. With the right equipment, SSEPs can be detected and changes in the evoked potential can be monitored to assess changes in nerve function. In an exemplary embodiment, the EPDD 140 uses the recording electrodes 112 to detect signals generated from the patient, including SSEPs. The EPDD 140 of some embodiments includes hardware, software, or a combination thereof to selectively record and process the detected signal to generate a meaningful signal for display. In order to produce and display meaningful data, the recorded signal should be free or substantially free of interference, for example, interference caused by electric surgical devices.

INTRODUCTION

Conventionally, the recorded signal of prior art evoked potential monitoring systems includes a target signal (e.g., an evoked potential) and random background noise, including EEG signals. At various times during surgery, the recorded signal may also include non-random high frequency electrical interference caused by electric tools or other devices used during surgery. The interference within the recorded signal can greatly distort the signal such that, even with processing, it is not an accurate representation of the target evoked potential.

Accordingly, in order for the processed signal to be most meaningful and the monitoring to be most effective, it would be beneficial if the recorded and/or processed signal was free or substantially free of significant noise and interference. This is a particular concern for evoked potentials, because even the presence of a little noise can dramatically reduce the signal-to-noise ratio due to the small size of evoked potentials. Evoked potentials, such as, for example, SSEPs, are small bioelectric signals with amplitudes as small as one microvolt or less. In comparison, the amplitude of many other recorded biological signals, such as EEG, EMG, and ECG, tend to be much larger. A typical EEG is usually 10 or more microvolts, EMG is one or more millivolts and an ECG signal can be hundreds of millivolts. The relative size of these other biological signals has meant that acquiring and monitoring such signals has been much easier to incorporate into standard surgical practice. In contrast, despite the clinical utility of evoked potentials, their small size has limited their use to specialized surgeries that justify having a technologist and/or neurologist present.

Due to their small size, recording evoked potentials reliably with existing prior art technology is difficult and requires a person with expertise in the practice to ensure that electrical interference is minimized. The smaller the biological signal, the more important it is to limit the noise contamination of the recording. Noise is produced when other electrical signals are picked up by, and coupled into, the recording circuits of the monitoring system. This contaminating noise can occur at any point along the acquisition circuit, including within the patient, at the site of the electrodes, within the cables carrying the unamplified signals, and at the location of signal amplifiers.

To record evoked potentials in an electrically noisy environment such as the operating room, surgical technologists currently employ a myriad of techniques to increase the signal-to-noise ratio of the evoked potential.

For example, many employ a signal averaging technique developed by Dawson in 1954. The signal averaging technique increases the signal to noise ratio by averaging time-locked stimulus-triggered sweeps. Dawson's signal averaging technique relies on the fact that evoked potential waveforms occur with a constant latency following each stimulus (barring changes in nervous system health or functionality), whereas most noise is random and will eventually average to near zero levels after successive stimuli. The signal averaging technique is helpful, for example, in reducing the effect of electroencephalogram (EEG) noise in the processed signal. The EEG is a relatively random signal arising from activity in the outer layers of the cortex. Accordingly, to extract evoked potential waveforms from the background noise, the surgical technologist generally uses an IONM system that applies successive time-locked stimuli. Multiple stimulus time locked recording epochs are averaged together. For example, IONM systems may stimulate peripheral nerves at a frequency of 2 to 5 Hz, and waveforms are acquired and averaged for analysis when 100 to 500 stimuli have been delivered.

Unfortunately, in a surgical setting, not all electrical interference is random, and some interference is so large that it cannot be removed via signal averaging or other currently available filtering techniques. In particular, a substantial amount of interference may be generated by electric surgical tools. The most common interference comes from the Electrosurgical Unit (ESU), also known as an RF knife or Bovie, used to cut and cauterize tissue in the operating room. When an ESU is enabled, typically there is a large amount of very high frequency content interference mixed with the biosignals of interest. This interference is often non-random and so large that the system is unable to remove this interference using the normal means of averaging the most recent sweep with other time locked sweeps.

In order for intraoperative neurophysiologic monitoring or other electrophysiological monitoring to be effective, it is desirable to keep the ESU-generated interference out of the signal of interest. Current means of ignoring ESU-generated interference have significant shortcomings. For example, currently, the most common method of keeping the ESU-generated interference out of the signal of interest is a mental process, performed by a neuro-monitoring specialist, which compares the displayed signal to a maximum positive or negative value of an analog-to-digital converter (ADC) in the system. In particular, many specialists in the field will simply assume a signal is contaminated with noise from the ESU and reject or disregard the signal if it gets within a particular threshold value, for example, 95%, of the maximum positive or negative value of the system's ADC.

Such an approach is lacking in sensitivity and specificity. Low levels of ESU interference may avoid rejection and still be present in the signal, and lowering the filter level to capture these low levels of ESU interference may cause rejection of normal evoked potential signals too and increase the time required to obtain a good SSEP waveform. Other specialists mentally disregard changes to waveforms that are observed within a time frame following the use of an ESU. Still other technologists turn off signal acquisition manually when an ESU is in use. This can be a tedious process since ESUs are used frequently during surgery to cut and cauterize tissue, and this process can result in missed changes in nervous system functioning, if signal acquisition remains off for too long and the changes occur during the time that the signal acquisition is in the off mode.

An alternate method to remove the ESU interference from a signal is to look at the frequency content of the signal coming from the patient. The ESU interference has an output frequency of between 200 kHz and 6 MHz. This is dramatically different from the biosignal of interest which has a frequency of less than 10 kHz. However, in typical evoked potential monitors, there is no ability to separately detect signals having frequencies as high as ESU-generated interference, because there are low-pass hardware filters in the signal path. These systems are not intended to view such high frequency content. Given the typical signals of interest, the systems are generally constructed such that there is no means for looking at signals with frequency content substantially higher than 10 kHz.

The above-described human judgment-based approaches to ESU interference "filtering" are error-prone and lacking in precision and accuracy. Additionally, as IONM devices become used in more surgeries, there will not be enough neuro-monitoring specialists to attend to each surgery. For this and other reasons, more automated IONM devices, if effective, could be desirable. The development of automated IONM devices is limited though, in part, by the need for improved interference rejection methods. There is a need for signal filtering methods that are not based on human judgment. Accordingly, in order to facilitate automation of IONM devices and improve the accuracy and precision of displayed evoked potential waveforms, improved biosignal-isolating techniques are needed.

Accordingly, the EPDD 140 of various embodiments provided herein, includes circuitry, a processor, and memory with instructions stored therein, which together function to prevent acquisition of random noise and non-random electrical interference, including ESU-caused interference, and produce a processed waveform representative of a patient's evoked potentials. The system 100 of various embodiments may include one or more features intended to improve the sensitivity and specificity of signal filtering. Various exemplary features are described below.

Methods and Components for Minimizing Noise in a Recorded Signal

In various embodiments, the specialized system 100 can be programmed to perform the well-known signal averaging techniques developed by Dawson to reduce the presence of random noise within the processed signal.

Additionally or alternatively, various embodiments of the system disclosed herein (such as, for example, the depicted system 100) include one or more methods or means of automatically managing and minimizing noise contamination within the recorded signal in order to automatically generate reliable data. Specifically, in various embodiments, the system (such as system 100) is configured to automatically detect when a high-noise generating device, such as an ESU, is in operation. In some embodiments, the system temporarily suspends data acquisition and/or grounds all received signals during the operation of an ESU. ESUs cut and cauterize tissue by applying electrical energy from a radio-frequency (RF) generator to the tip of the ESU. Thus, in an exemplary embodiment of the system 100, the EPDD 140 includes an RF receiver configured to receive radio frequencies emitted from nearby electric surgical devices, such as an ESU. In some embodiments, the RF receiver is included within an amplifier system in the EPDD 140. In some embodiments, when a threshold level of high frequency RF signals are detected by the RF receiver of the EPDD 140, the system suspends signal acquisition or signal processing.

In order to detect when a high frequency noise generating device, such as an ESU or other electric surgical tool, is in operation and temporarily suspend data acquisition, various embodiments provided herein include the addition of an alternative signal path to a typical evoked potential amplifier system.

Figure 2:
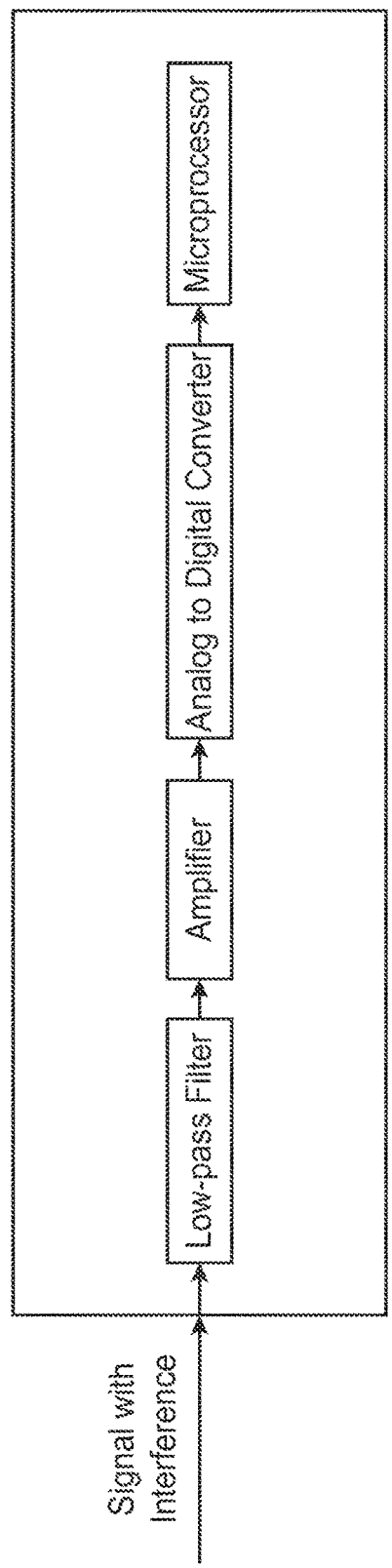
FIG. 2 depicts a block diagram of an amplifier system known in the prior art.

A conventional evoked potential amplifier system is provided in FIG. 2 for reference. Such an amplifier system is provided in at least some existing IONM systems. In the amplifier system, a detected signal, which includes a target signal and high frequency interference, enters a low pass filter. Only signal frequencies below a given threshold, such as, for example, 10 kHz, are allowed to pass. The portion of the signal that passes through continues on to an amplifier where the signal is amplified in magnitude, for example, by 100×, 1000×, or 10000×. This amplified signal is converted into a digital signal and passed to a microprocessor for further signal processing and/or analysis. Problematically, noise fluctuates in frequency, even from typically high-frequency devices such as ESUs. Accordingly, the low pass filter is insufficient to remove all noise from the detected signal, resulting in noise entering the amplifier. While evoked potentials have amplitudes as small as 1 millivolt, the noise from electric surgical tools tends to have much greater amplitudes. As a result, noise entering the amplifier can quickly saturate the amplifier and distort the signal passed through to the microprocessor.

Figure 3:
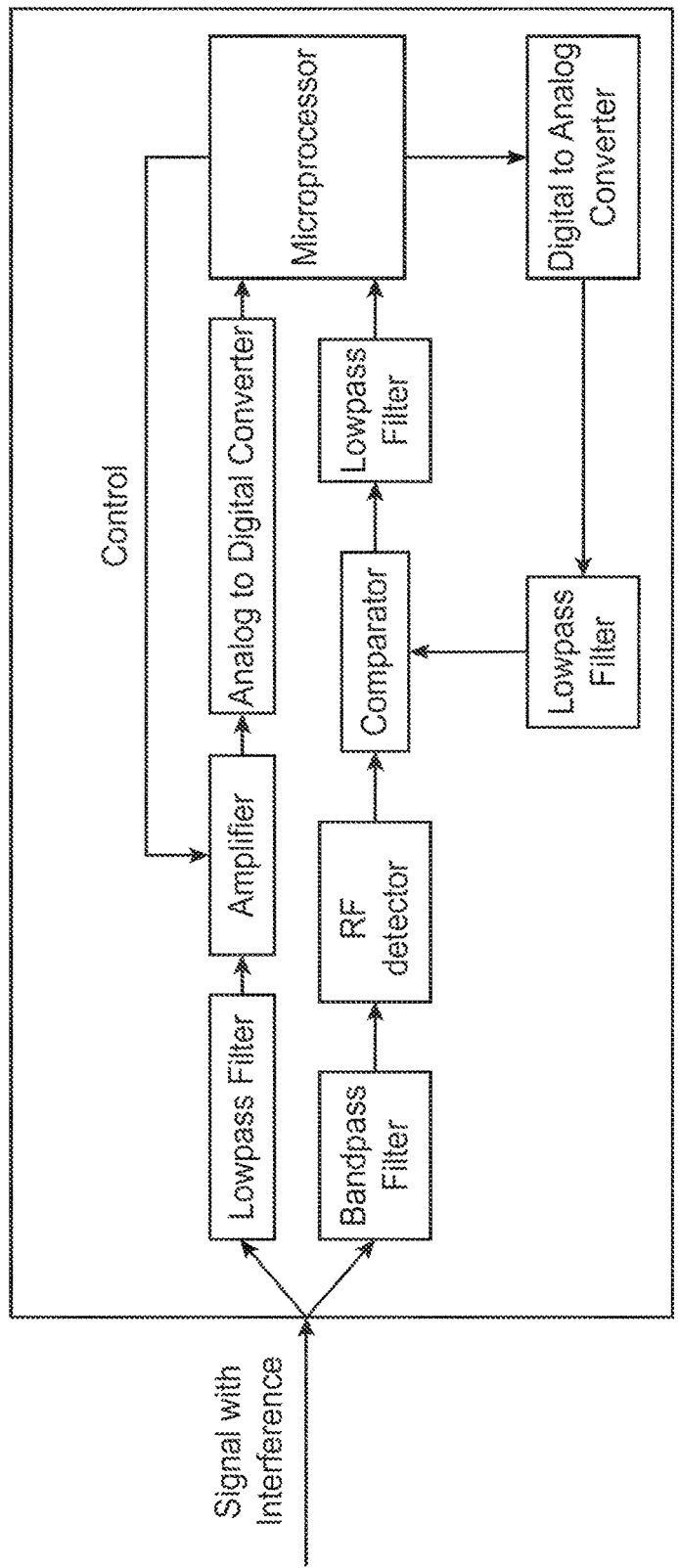
FIG. 3 depicts a block diagram of one embodiment of an amplifier system constructed in accordance with the principles of the present disclosure.

One embodiment of a modified evoked potential amplifier system, constructed in accordance with the principles of the present disclosure, is shown in FIG. 3. The block diagram of FIG. 3 depicts various functional or structural components present within an evoked potential amplifier system. The depicted amplifier system may be included, for example, within or coupled to the evoked potential detection device (EPDD) 140 of FIG. 1 for the purposes of filtering and amplifying the detected signal. While the depicted embodiment and other embodiments described herein are often referred to as improved "evoked potential amplifier systems," it will be appreciated by those skilled in the art that the improved amplifier systems described herein may be used to filter and amplify any desired biosignal.

In the amplifier system of FIG. 3, a power splitter (not shown) and an alternate signal path are provided to separate the signal of interest from high frequency interference. The power splitter of at least some embodiments directs low power signals, such as those in the 0.1-100 millivolt range, to a primary path (shown in FIG. 3 as the upper path). Such signals are primarily composed of the target signals (e.g., evoked potentials). Higher power signals (i.e., signals having a larger amplitude) are directed to an alternative path (shown in FIG. 3 as the lower path). The lower path is configured to enable detection of high frequency noise. For example, the lower path includes a comparator electrically coupled to a microprocessor. The comparator compares the level of high frequency contamination in the lower path signal with a threshold level set by a user via the microprocessor. When the lower path signal is larger than the threshold level, the comparator outputs a signal to the coupled microprocessor. Said signal acts as an alert, alerting the microprocessor that high frequency interference is present. When high frequency noise is detected, the microprocessor delivers an interrupt signal via a Control line to the amplifier of the primary path. The interrupt signal causes the amplifier to temporarily suspend operations. Such a system prevents the amplifier of the primary path from getting saturated each time an electric surgical tool is used during surgery.

While the circuit of FIG. 3 is an improvement over the evoked potential amplifier systems present within conventional IONM systems, it may not be desirable in all settings. Since the evoked potential signals are very small, any additional circuitry, such as a power splitter to split the recorded signal, on the signal line going to the first amplifier stage may decrease the quality of the amplified signal. Instead, an alternate signal line to the patient (as shown and described with respect to FIG. 4) may be preferred.

Figure 4:
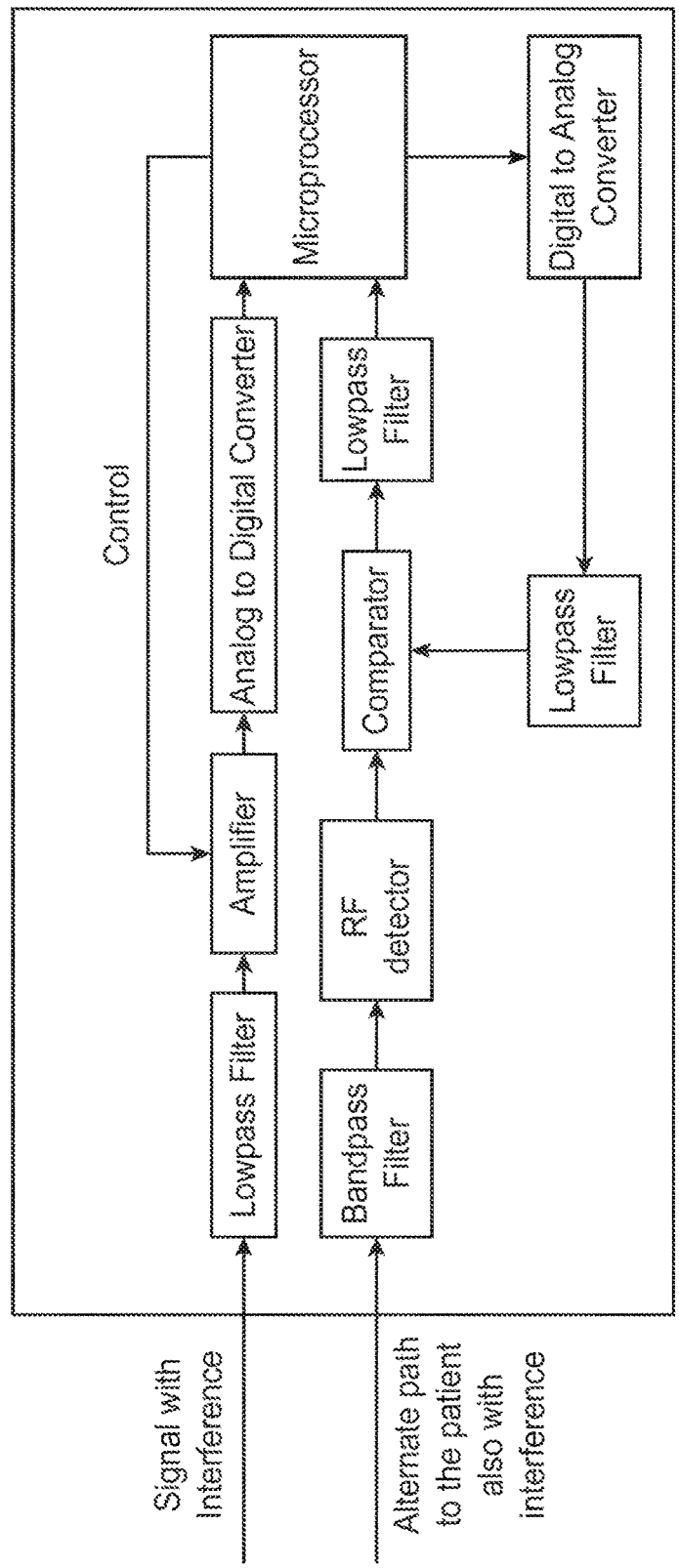
FIG. 4 depicts a block diagram of another embodiment of an amplifier system constructed in accordance with the principles of the present disclosure.

FIG. 4 provides a block diagram of the various functional and/or structural components of one embodiment of a preferred evoked potential amplifier system. As with FIG. 3 above, the amplifier system described herein may be used to amplify any desired biosignal. The depicted components may be included, for example, within the circuitry of the evoked potential detection device (EPDD) 140 of FIG. 1 in order to filter and amplify the detected signal.

In the depicted embodiment, there are two possible paths of travel for interference from electric surgical tools to enter the amplifier system: (1) through the air as a radio frequency electro-magnetic wave, or (2) as a conducted signal. In some embodiments, the preferred path is along an unshielded wire that is capacitive coupled to the patient. The unshielded wire may pick up electro-magnetic waves through the air and the capacitive coupled line may pick up the conducted signal.

As shown, the alternative (e.g., lower) path depicted in FIG. 4 includes a band pass filter or high pass filter, an RF detector, a comparator, one or more low pass filters, a microprocessor, and a digital to analog converter.

In the depicted embodiment, the band pass filter may be configured to allow signals to pass through only when they are within the typical range of signals generated by electric surgical tools. The band pass filter on the alternative signal line may be formed of, or include, one or more inductors, capacitors, or a combination thereof, configured to pass the frequency band of interest while eliminating signals outside the frequency band of interest. In some embodiments, the band pass filter may be a Butterworth filter, a Chebyshev filter, a Bessel filter, or any other type of filter known to a skilled person. In some embodiments, the band pass filter may be an active filter. In at least some embodiments, the frequency band of interest is, for example, 200 kHz to 6 MHz. In an alternative embodiment, a high pass filter is provided, which allows passage of signals above a given frequency, such as, for example, above 200 kHz.

Figure 5:
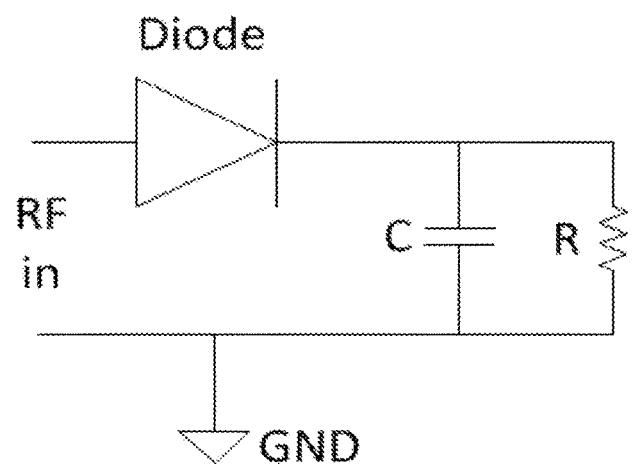
FIG. 5 depicts a circuit diagram of one embodiment of a radiofrequency detector present within the amplifier system of FIG. 4.

In various embodiments, signals passing through the first filter of the alternative pathway enter a radiofrequency (RF) detector. In some non-limiting embodiments, the RF detector is formed of an ultrafast diode (such as, for example, the Vishay ES07D-GS08), a capacitor connected to ground, and a parallel shunt resistor connected to ground, as depicted in FIG. 5. In some embodiments, when a threshold level of RF signals are detected, the signal in the alternative path enters a comparator.

The comparator may be a linear device such as, for example, the Texas Instruments differential comparator LM393. The comparator has two "legs" or signal sources, and the comparator is configured to compare signals from the two legs to identify which signal is larger (e.g., which signal has a greater amplitude). In some embodiments, one leg of the comparator is connected to the output from the RF detector. In some embodiments, the other leg is electrically connected to the output from a Digital to Analog Converter, which, in turn, is connected to the output from the microprocessor. In such embodiments, the second leg is adjustable, for example, adjustable in software. The comparator compares the level (e.g., the power level) of high frequency contamination in the recorded signal with a threshold level (e.g., a threshold power level) set by a user via the microprocessor. The user may adjust the threshold level using the microprocessor. When the recorded signal in the alternative path is larger than the threshold level set by the user, the signal output of the comparator (which may be filtered by a low pass filter) acts as an alert to the microprocessor, alerting the microprocessor that high frequency interference is present.

Upon receiving a signal alerting the microprocessor of high frequency interference, the microprocessor may reject the data received from the analog to digital converter on the primary path. The microprocessor may also send an interrupt signal along a control line to the amplifier of the primary path, said interrupt signal causing the amplifier to temporarily suspend operation. Such steps may protect the hardware from damage and avoid data acquisition of distorted signals. In some embodiments, the amplifier may suspend operations for 10 seconds. In other embodiments, the amplifier may suspend operations for 5 seconds, 60 seconds, or any value therebetween. In various embodiments, the amplifier may suspend operations until the comparator no longer detects that the signal from the RF detector is greater than the threshold level set by the user or until any defined time after that occurs. In some embodiments, when an electric surgical tool is no longer in use (i.e., when the signal from the RF detector is no longer greater than the threshold level set by the user), the microprocessor will no longer send an interrupt signal to the amplifier of the primary path and the amplifier will automatically resume functioning. This control acts as, or similar to, a reverse squelch, only allowing a signal through the primary path if the high frequency content is determined via the alternative path to be sufficiently low. A squelch normally only allows a signal through that is sufficiently large.

In an alternate design, the output of the comparator can go directly to the control line using logic circuitry instead of a software-mediated microprocessor. This may reduce the latency by a few microseconds and better protect the system from interference.

In various embodiments, if the comparator senses high frequency content that is too high, the microprocessor may reject that data and protect the amplifiers from any ill effects that could be caused by high frequency signals. The microprocessor may adjust the level of high frequency interference allowed into the signal so that the system can still be used even if there is always noise in the environment. The system can be adjusted to quiet operating rooms and get very clean signals quickly and still operate in noisy environments where the number of averages may be higher. In various embodiments, the microprocessor rejects any averages that are in the process of being acquired upon detection of high frequency noise (e.g., noise with a frequency above 200 kHz). Since it is possible that there may be other types of interference in addition to interference from electric surgical tools, the established level detection methods may be operated in parallel with the frequency specific system and method described herein.

Figure 6:
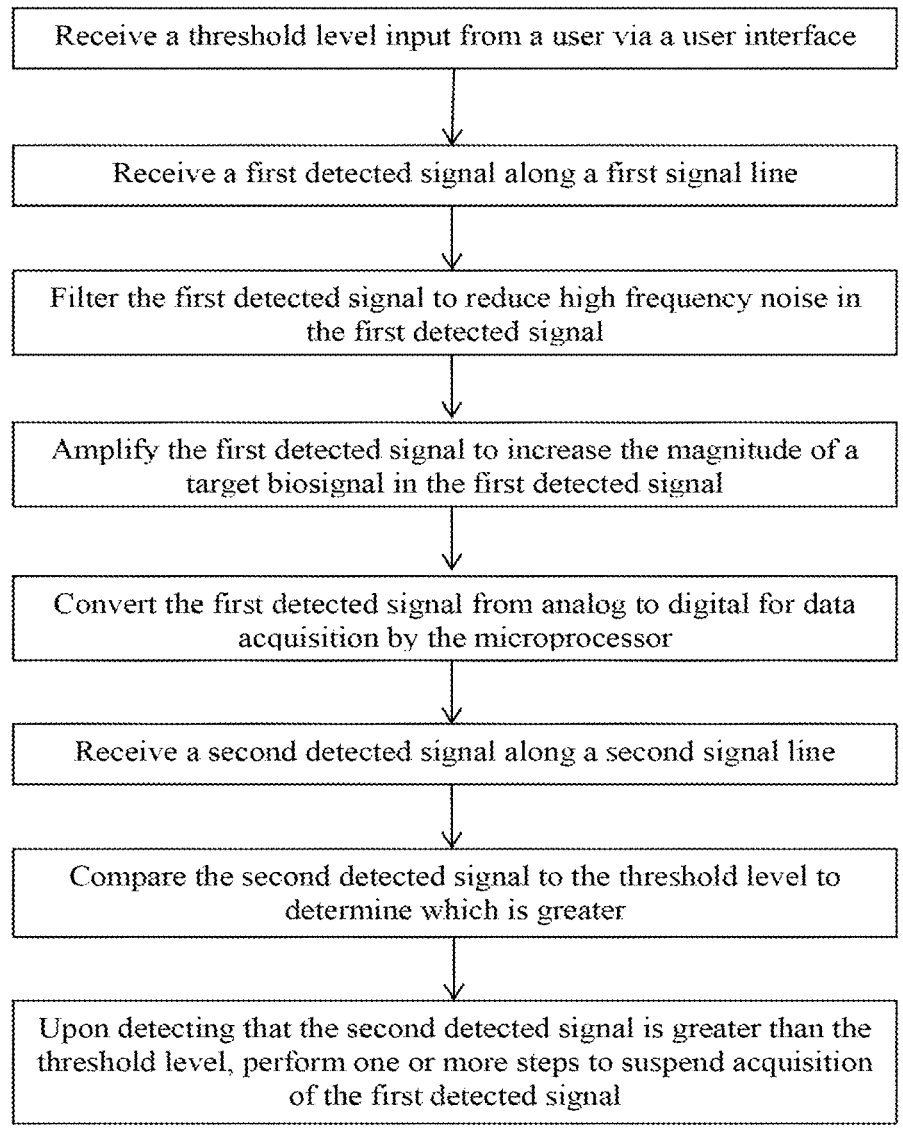
FIG. 6 depicts a flow chart of one embodiment of a method performed in accordance with the principles of the present disclosure.

One method performed by an amplifier system, such as the amplifier system of FIG. 4, is provided in FIG. 6. As shown, at block 602, in some embodiments, the amplifier system receives a threshold level input from a user via a user interface. The user interface may form part of, or be connected to, a microprocessor. The threshold level may be set, for example, to match a known power level of an ESU or other electrical equipment present in an operating room.

At block 604, the amplifier system receives a first detected signal along a first signal line. The first detected signal includes a target biosignal and high frequency noise. At block 606, the amplifier system filters the first detected signal to reduce the high frequency noise in the first detected signal. Such filtering may be performed, for example, by a low pass filter. At block 608, the amplifier system amplifies the first detected signal to increase a magnitude of the target biosignal. Such amplification may be performed by an amplifier. At block 610, the amplifier system converts the first detected signal from analog to digital for data acquisition by the microprocessor.

At block 612, the amplification system receives a second detected signal along a second signal line, such as, for example, an unshielded wire capacitively coupled to a patient. Like the first detected signal, the second detected signal also includes the target biosignal and the high frequency noise. At block 614, the amplification system compares the second detected signal to the threshold level to determine whether the second detected signal or the threshold level is greater. For example, the amplitude or power level of the second detected signal may be compared to the threshold level. In some embodiments, the second detected signal is filtered via a band pass filter or high pass filter and accumulated and/or averaged by an RF detector before being compared to the threshold level.

As shown at block 616, upon detecting that the second detected signal is greater than the threshold level, the amplifier system may perform one or more steps to suspend acquisition of the first detected signal. For example, the amplifier system may: suspend acquisition and storage of digital data at the microprocessor, and/or deliver an interrupt signal along a Control line to an amplifier within the first signal line, wherein the interrupt signal causes the amplifier to temporarily suspend operation. In some such embodiments, the amplifier suspends operation for approximately 5 to approximately 60 seconds. In other embodiments, the amplifier suspends operations until the second detected signal is no longer detected to be greater than the threshold level, or until a defined time thereafter. In other embodiments, the amplifier suspends operation until transmission of the interrupt signal ceases.

The components and methods described above can be included in, and performed by, any biosignal monitoring apparatus, such as, for example, the evoked potential detection device (EPDD) 140 of FIG. 1. In various embodiments, the components and methods described above result in the generation of clean processed signals that are free or substantially free of high frequency interference. As described above, in various embodiments, the components and methods of the present technology cause a biosignal monitoring device to automatically suspend data acquisition and amplifier operations when high frequency signals are detected. Thus, in various embodiments, the components and methods of the present technology cause a biosignal monitoring device to automatically suspend data acquisition and amplifier operations any time an ESU or other electric surgical tool is in use. The components and methods may also cause the biosignal monitoring device to automatically resume data acquisition and amplifier operations when the electric surgical tool is no longer in use. In such a manner, the components and methods are able to keep high frequency interference out of the processed signal. Accordingly, the processed signal that is generated in various embodiments is an accurate and precise representation of a patient's biosignals. By generating clean processed signals, biosignal monitoring apparatuses of the present technology are able to monitor a patient's biosignals for changes. The biosignals may be monitored by a healthcare professional viewing a display screen that displays the processed biosignals, and/or the biosignal monitoring device may automatically monitor the biosignals for changes. In some embodiments, changes in latency, amplitude, and/or morphology may be indicative of an injury to the central or peripheral nervous system. As described, for example, in U.S. Pat. No. 8,731,654 to Johnson et al., the disclosure of which is herein incorporated by reference in its entirety, the monitoring devices of some embodiments are configured to automatically identify positioning effect in a patient based on changes in the patient's evoked potentials. Such embodiments are possible when the processed signal is an accurate and precise representation of the patient's biosignals.

The Microprocessor

In preferred embodiments, the EPDD 140 of FIG. 1 includes a processor, connected circuitry, and memory storing instructions, which together operate to amplify and filter the detected signal as described above. In various embodiments, the memory, processor, and circuitry are components of a specialized computer, and in at least some such embodiments, the EPDD 140 forms part of, is coupled via a wired or wireless connection to, and/or includes said computer. Additionally, in some embodiments, the system 100 includes one or more user interfaces to receive inputs from a user and provide outputs to the user. Such user interfaces may form part of the computer or may be in electrical or wireless communication with the computer. A discussion of the components of an example computer are provided below. The discussion is intended to be non-limiting as one skilled in the art will appreciate that any number of computer architectures may be suitable for use in, with, or as the evoked potential detection device. In some embodiments, the described computer forms the microprocessor shown in FIG. 3 and/or FIG. 4.

Figure 7:
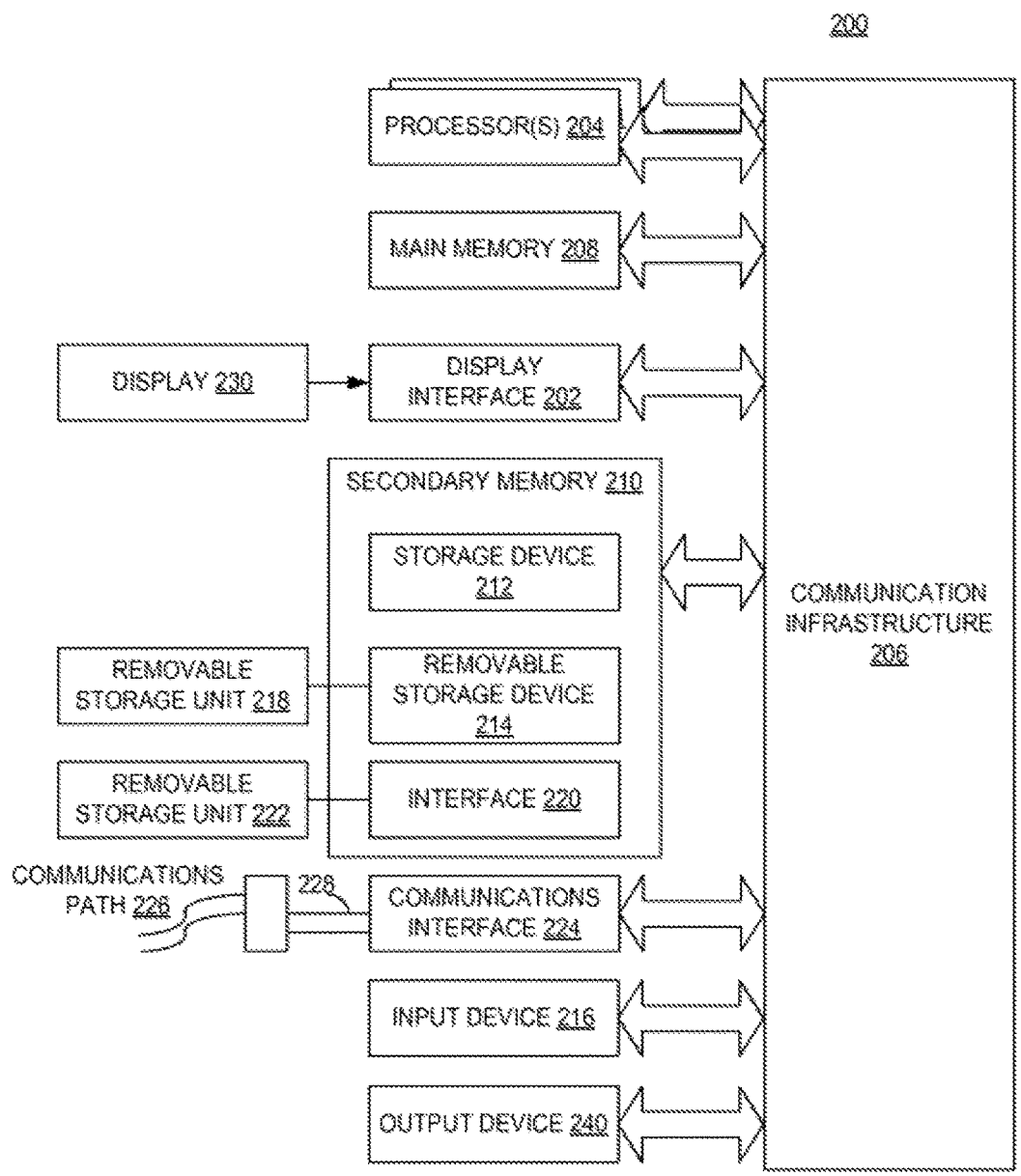
FIG. 7 depicts a functional block diagram of one embodiment of a computer system that may be used in association with, in connection with, and/or in place of certain embodiments of the systems and components described herein.

FIG. 7 depicts a block diagram of one example embodiment of a computer system that may form part of any of the systems described herein. Specifically, FIG. 7 illustrates an example computer 200, which may run an operating system such as, for example, MICROSOFT® WINDOWS® NT/98/2000/XP/CE/7/VISTA/RT/8, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., iOS or Mac/OS from APPLE® Corporation of Cupertino, Calif., U.S.A., or any of various versions of UNIX® (a trademark of the Open Group of San Francisco, Calif., USA) including, e.g., LINUX®, HPUX®, IBM AIX®, and SCO/UNIX®, or Android® from Google®, Inc. of Mountain View, Calif., U.S.A., etc. Such operating systems are provided for example only; the system embodiments described herein may be implemented on any appropriate computer system running any appropriate operating system.

The computer system 200 may include one or more processors, such as processor(s) 204. The processor(s) 204 may be connected to a communication infrastructure 206 (for example, a communications bus, cross-over bar, or network, etc.). Various software embodiments may be described in terms of this example computer system. After reading this description, it will become apparent to a person skilled in the relevant art how to implement the described methods using other computer systems and/or architectures. Computer system 200 may include a display interface 202 to forward graphics, text, and other data, etc., from the communication infrastructure 206 for display on the display unit 230.

The computer system 200 may also include, e.g., but may not be limited to, a main memory 208, random access memory (RAM), and a secondary memory 210, etc. The secondary memory 210 may include, for example, (but may not be limited to) a hard disk drive 212 and/or a removable storage drive 214, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 214 may read from and/or write to a removable storage unit 218 in a well-known manner. Removable storage unit 218 may represent, for example, a floppy disk, a magnetic tape, an optical disk, a magneto-optical disk, a compact disk, a flash memory device, etc. which may be read from and written to by removable storage drive 214. As will be appreciated, the removable storage unit 218 may include a computer usable storage medium having stored therein computer software and/or data.

In alternative exemplary embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as, e.g., but not limited to, those found in some video game devices), a removable memory chip (such as, e.g., but not limited to, an erasable programmable read only memory (EPROM)), or programmable read only memory (PROM) and associated socket, and other removable storage units 222 and interfaces 220, which may allow software and data to be transferred from the removable storage unit 222 to the computer system 200.

The computer 200 may also include an input device 216 such as, for example, a mouse or other pointing device such as a digitizer, a touchscreen, a microphone, a keyboard, and/or other data entry device. The computer 200 may also include output devices 240, such as, for example, a display 230 and/or display interface 202. The computer 200 may include input/output (I/O) devices such as a communications interface 224, a cable 228, and/or a communications path 226, etc. These devices may include but are not limited to a network interface card and modems. The communications interface 224 may allow software and data to be transferred between the computer system 200 and external devices. Examples of a communications interface 224 include, for example, a modem, a network interface (such as, e.g., an Ethernet card), a communications port, a Personal Computer Memory Card International Association (PCMCIA) slot and card, etc. Software and data transferred via the communications interface 224 may be in the form of signals 228 which may be electronic, electromagnetic, optical, or other signals capable of being received by the communications interface 224. These signals 228 may be provided to the communications interface 224 via, for example, a communications path 226 such as a channel. This channel 226 may carry signals 228, for example propagated signals, and may be implemented using, for example, wire or cable, fiber optics, a telephone line, a cellular link, a radio frequency (RF) link and other communications channels, etc.

In various embodiments described herein, wired networks may include any of a wide variety of well-known means for coupling voice and data communications devices together. In various embodiments described herein, wireless network types may include, but are not limited to, for example, code division multiple access (CDMA), spread spectrum wireless, orthogonal frequency division multiplexing (OFDM), 1G, 2G, 3G, or 4G wireless, Bluetooth, Infrared Data Association (IrDA), shared wireless access protocol (SWAP), "wireless fidelity" (Wi-Fi), WIMAX, and other IEEE standard 802.11-compliant wireless local area network (LAN), 802.16-compliant wide area network (WAN), and ultra-wideband (UWB) networks, etc.

Some embodiments may include or otherwise make reference to WLANs. Examples of a WLAN may include a shared wireless access protocol (SWAP) developed by Home radio frequency (HomeRF), and wireless fidelity (Wi-Fi), a derivative of IEEE 802.11, advocated by the wireless Ethernet compatibility alliance (WECA). The IEEE 802.11 wireless LAN standard refers to various technologies that adhere to one or more of various wireless LAN standards. An IEEE 802.11 compliant wireless LAN may comply with any of one or more of the various IEEE 802.11 wireless LAN standards including, for example, wireless LANs compliant with IEEE std. 802.11a, b, d, g, or n, such as, e.g., but not limited to, IEEE std. 802.11 a, b, d, g, and n (including, e.g., but not limited to IEEE 802.11g-2003, etc.), etc.

Some embodiments described herein are directed to the apparatuses and/or devices for performing the operations described herein. Such an apparatus may be specially constructed for the desired purposes, or it may comprise a general purpose device selectively activated or reconfigured by a program stored in the device to perform the specialized purpose.

In one example embodiment, the EPDD 140 sends data to an external user interface, such as a monitor, smartphone, or tablet, for display to the user. The communications interface 224 allows data to be transferred between the computer system 200 and the external user interface. In some embodiments, the communications interface 224 is a USB port or other port configured to receive a cable connected to the external user interface. In other embodiments, the communications interface 224 is a cellular, Wi-Fi, or RF antenna or other interface for wireless communications. The antenna of various embodiments acts both a transmitter and receiver.

Other embodiments described herein are directed to instructions stored on a machine-readable medium, which may be read and executed by a computing platform to perform operations described herein. A machine-readable medium may include any mechanism for storing or transmitting information in a form readable by a machine (e.g., a computer). For example, an exemplary machine-readable storage medium may include: read only memory (ROM); random access memory (RAM); magnetic disk storage media; optical storage media; magneto-optical storage media; flash memory devices; other exemplary storage devices capable of storing electrical, optical, acoustical, or other form of propagated signals (e.g., carrier waves, infrared signals, digital signals, etc.) thereon, and others. Computer programs (also called computer control logic), may include object oriented computer programs, and may be stored in main memory 208 and/or the secondary memory 210 and/or removable storage units 214, also called computer program products. Such computer programs, when executed, may enable the computer system 200 to perform the features of the present technology. In particular, the computer programs, when executed, may enable the processor or processors 204 to provide a method for filtering and processing an evoked potential signal according to an exemplary embodiment.

Another exemplary embodiment is directed to a computer program product comprising a computer readable medium having control logic (computer software) stored therein. The control logic, when executed by the processor 204, may cause the processor 204 to perform functions described herein. In other embodiments, various functions described herein may be implemented primarily in hardware using, for example, but not limited to, hardware components such as application specific integrated circuits (ASICs), an integrated circuit board with various circuit components, or one or more state machines, etc. Implementation of the hardware state machine so as to perform the functions described herein will be apparent to persons skilled in the relevant art. In some embodiments, signal filtering, processing, and other described functions may be implemented using one or a combination of any of hardware, firmware, software, etc.

The computer program mediums and computer readable mediums described herein may provide software to computer system 200. The software includes a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

According to an exemplary embodiment, exemplary methods set forth herein may be performed by an exemplary one or more computer processor(s) adapted to process program logic, which may be embodied on an exemplary computer accessible storage medium, which when such program logic is executed on the exemplary one or more processor(s), may perform such exemplary steps as set forth in the exemplary methods.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A method performed by an amplifier system within a biosignal monitoring device, the method comprising:
   receiving a threshold level input from a user via a user interface;
   receiving a first detected signal along a first signal line, wherein the first detected signal comprises a target biosignal and high frequency noise;
   filtering the first detected signal to reduce the high frequency noise in the first detected signal;
   amplifying the first detected signal to increase a magnitude of the biosignal; converting the first detected signal from analog to digital for data acquisition by a microprocessor;
   receiving a second detected signal along a second signal line, wherein the second detected signal comprises the target biosignal and the high frequency noise;
   comparing the second detected signal to the threshold level to determine whether the second detected signal or the threshold level is greater; and
   upon detecting that the second detected signal is greater than the threshold level, performing one or more steps to suspend acquisition of the first detected signal.

2. The method of claim 1, wherein the one or more steps performed to suspend acquisition of distorted signals comprises: suspending acquisition and storage of digital data by a microprocessor, wherein the digital data is received from an analog to digital converter of the first signal line, and wherein the digital data is a digitized first detected signal.

3. The method of claim 1, wherein the one or more steps performed to suspend acquisition of distorted signals comprises: transmitting an interrupt signal along a control line to an amplifier within the first signal line, wherein the interrupt signal causes the amplifier to temporarily suspend operation.

4. The method of claim 3, wherein the amplifier suspends operation for approximately 5 to approximately 60 seconds.

5. The method of claim 3, wherein the amplifier suspends operations until the second detected signal is no longer detected to be greater than the threshold level, or until a defined time thereafter.

6. The method of claim 3, wherein the amplifier suspends operation until transmission of the interrupt signal ceases.

7. The method of claim 1, wherein the amplifier system comprises:
   an evoked potential detection device including at least one data processor and at least one memory storing instructions for stimulating a peripheral nerve and recording one or more detected signals, the evoked potential detection device further comprising:
      a first signal pathway and a second signal pathway coupled with the evoked potential detection device, each signal pathway having an input for the first detected signal, wherein the first signal pathway is configured to amplify the target signal and comprises, in order:
         a low pass filter,
         an amplifier,
         an analog to digital converter, and
         a microprocessor;
      wherein the second signal pathway is configured to detect the high frequency interference and comprises:
         a band pass filter or high pass filter electrically coupled to a radiofrequency detector,
         a comparator,
         a digital to analog converter, and
         the microprocessor of the first signal pathway;
   wherein the comparator is configured to compare a first amplitude of the first detected signal entering from a first leg and a second amplitude of the second detected signal entering from a second leg, the first leg of the comparator being electrically coupled to an output from the radiofrequency detector, and the second leg being electrically coupled via the digital to analog converter to an output from the microprocessor;
   wherein the microprocessor is electrically coupled to an output from the comparator and is configured to detect the presence of high frequency interference within the first detected signal when the first amplitude is greater than the second amplitude; and
   wherein the evoked potential detection device is configured to temporarily suspend data acquisition upon detection of the high frequency interference.

8. The method of claim 7, wherein the second detected signal is a threshold signal set by a user interacting with the microprocessor via a user interface.

9. The method of claim 7, wherein the amplifier system further comprises a control line electrically connecting the microprocessor to the amplifier, wherein the control line is configured to deliver an interrupt signal to the amplifier upon detection of high frequency interference.

10. The method of claim 7, wherein the amplifier system further comprises one or more low pass filters positioned between the comparator and the microprocessor.

11. The method of claim 7, wherein the band pass filter of the second signal pathway comprises one or more inductors, capacitors, or a combination thereof, configured to pass a frequency band of interest while eliminating signals outside the frequency band of interest.

12. The method of claim 11, wherein the frequency band of interest is 200 kHz to 6 MHz.

13. The method of claim 7, wherein the radiofrequency detector comprises an ultrafast diode, a capacitor connected to ground, and a parallel shunt resistor connected to ground.

14. The method of claim 7, wherein the target signal is a biological signal.

15. The method of claim 14, wherein the biological signal is an evoked potential.

16. A method for detecting changes in nerve functioning within a subject, comprising:
   receiving a biosignal from a patient, as an input at a biosignal detection device;
   producing a processed signal having minimal electronic interference or background noise contaminating the processed signal, wherein such a processed signal is produced by reducing, blocking, ignoring, or disregarding detected signals received when high frequency electronic interference or background noise is present;
   comparing at least two processed signals received at different time periods;
   identifying a change in the biosignal based upon the comparison of the at least two processed signals; and
   temporarily suspending data acquisition upon identification of the change in the biosignal.

17. The method of claim 16, wherein the biosignal is an evoked potential.

18. The method of claim 16, further comprising detecting a nerve injury during a medical procedure based on changes observed between the at least two processed signals.

19. The method of claim 16, wherein the change in the biosignal comprises high frequency interference.

20. The method of claim 16, wherein the biosignal detection device suspends operations until the change in the biosignal is no longer detected, or until a defined time thereafter.

* * * * *